(12) United States Patent
Metzger et al.

(10) Patent No.: US 7,017,582 B2
(45) Date of Patent: Mar. 28, 2006

(54) STIFFENING PHARYNGEAL WALL TREATMENT

(75) Inventors: Anja K. Metzger, Stillwater, MN (US); Brian J. Erickson, Woodbury, MN (US); John P. Sopp, Forest Lake, MN (US); Mark B. Knudson, Shoreview, MN (US); Timothy R. Conrad, Eden Prairie, MN (US)

(73) Assignee: Restore Medical Inc., St. Paul, MN (US)

( * ) Notice: Subject to any disclaimer, the term of this patent is extended or adjusted under 35 U.S.C. 154(b) by 199 days.

(21) Appl. No.: 10/237,149

(22) Filed: Sep. 6, 2002

(65) Prior Publication Data
US 2003/0149488 A1 Aug. 7, 2003

Related U.S. Application Data

(63) Continuation-in-part of application No. 10/066,967, filed on Feb. 4, 2002.

(51) Int. Cl.
*A61F 13/00* (2006.01)

(52) U.S. Cl. .................................. 128/898; 623/23.73

(58) Field of Classification Search ............... 606/196, 606/204.45; 128/898, 848
See application file for complete search history.

(56) References Cited

U.S. PATENT DOCUMENTS

| | | | |
|---|---|---|---|
| 3,998,209 A | 12/1976 | Macvaugh | |
| 4,803,075 A | 2/1989 | Wallace et al. | |
| 4,830,008 A | 5/1989 | Meer | |
| 4,978,323 A | 12/1990 | Freedman | |
| 5,046,512 A | 9/1991 | Murchie | |
| 5,052,409 A | 10/1991 | Tepper | |
| 5,133,354 A | 7/1992 | Kallok | |
| 5,158,080 A | 10/1992 | Kallok | |
| 5,176,618 A | 1/1993 | Freedman | |
| 5,178,156 A | 1/1993 | Takishima et al. | |
| 5,190,053 A | 3/1993 | Meer | |
| 5,204,382 A | 4/1993 | Wallace et al. | |
| 5,258,028 A | 11/1993 | Ersek et al. | |
| 5,284,161 A | 2/1994 | Karell | |
| 5,421,406 A | 6/1995 | Furusawa et al. | |
| 5,456,662 A | 10/1995 | Edwards et al. | |
| 5,494,029 A | 2/1996 | Lane et al. | |
| 5,514,131 A | 5/1996 | Edwards et al. | |
| 5,540,733 A | 7/1996 | Testerman et al. | |

(Continued)

FOREIGN PATENT DOCUMENTS

DE 44 12 190 A1 10/1995

(Continued)

OTHER PUBLICATIONS

Aboubakr, S. et al., "Long-term facilitation in obstructive sleep apnea patients during NREM sleep", *J Appl Physiol*, vol. 91, pp. 2751-2757 (Dec. 2001).

(Continued)

*Primary Examiner*—(Jackie) Tan-Uyen T. Ho
(74) *Attorney, Agent, or Firm*—Merchant & Gould P.C.

(57) ABSTRACT

A pharyngeal airway having a pharyngeal wall of a patient at least partially surrounding and defining the airway is treated by selecting an implant dimensioned so as to be implanted at or beneath a mucosal layer of the pharyngeal wall and extending transverse to said wall. The implant has mechanical characteristics for the implant, at least in combination with a fibrotic tissue response induced by the implant, to stiffen said pharyngeal wall to resist radial collapse. The implant is implanted into the pharyngeal wall transverse to a longitudinal axis of the airway.

29 Claims, 7 Drawing Sheets

U.S. PATENT DOCUMENTS

| | | | |
|---|---|---|---|
| 5,591,216 A | 1/1997 | Testerman et al. | |
| 5,669,377 A | 9/1997 | Fenn | |
| 5,674,191 A | 10/1997 | Edwards et al. | |
| 5,718,702 A | 2/1998 | Edwards | |
| 5,791,341 A | 8/1998 | Bullard | |
| 5,792,067 A | 8/1998 | Karell | |
| 5,792,478 A | 8/1998 | Lawin et al. | |
| 5,843,021 A | 12/1998 | Edwards et al. | |
| 5,853,004 A | 12/1998 | Goodman | |
| RE36,120 E | 3/1999 | Karell | |
| 5,897,579 A | 4/1999 | Sanders | |
| 5,922,006 A | 7/1999 | Sugerman | |
| 5,979,456 A | 11/1999 | Magovern | |
| 5,983,136 A | 11/1999 | Kamen | |
| 5,988,171 A | 11/1999 | Sohn et al. | |
| 6,098,629 A | 8/2000 | Johnson et al. | |
| 6,216,702 B1 | 4/2001 | Gjersøe | |
| 6,240,316 B1 | 5/2001 | Richmond et al. | |
| 6,250,307 B1 | 6/2001 | Conrad et al. | |
| 6,431,174 B1 * | 8/2002 | Knudson et al. | 128/898 |
| 6,748,950 B1 | 6/2004 | Clark et al. | |
| 2001/0037133 A1 | 11/2001 | Knudson et al. | |
| 2002/0049479 A1 | 4/2002 | Pitts | |
| 2004/0045556 A1 | 3/2004 | Nelson et al. | |
| 2004/0134491 A1 | 7/2004 | Pflueger et al. | |
| 2004/0139975 A1 | 7/2004 | Nelson et al. | |
| 2004/0149290 A1 | 8/2004 | Nelson et al. | |
| 2004/0153127 A1 | 8/2004 | Gordon et al. | |

FOREIGN PATENT DOCUMENTS

| | | |
|---|---|---|
| DE | 199 20 114 A1 | 11/2000 |
| EP | 0 706 808 A1 | 4/1996 |
| EP | 1 039 859 B1 | 12/2003 |
| JP | 11-33120 | 9/1999 |
| SU | 1553140 A1 | 3/1990 |
| WO | WO 01/19301 A1 | 3/2001 |
| WO | WO 01/23039 A1 | 4/2001 |
| WO | WO/2004/021869 A2 | 3/2004 |
| WO | WO/2004/021870 A2 | 3/2004 |

OTHER PUBLICATIONS

Badr, M. "Effect of ventilatory drive on upper airway patency in humans during NREM sleep", *Respiration Physiology*, vol. 103, No. 1, pp. 1-10 (1996).

Boot, H. et al., "Long-Term Results of Uvulopalatopharyngoplasty for Obstructive Sleep Apnea Syndrome", *Laryngoscope*. vol. 110, pp. 469-475 (Mar. 2000).

Boudewyns, A. et al., "Temperature-controlled Radiofrequency Tissue Volume Reduction of the Soft Palate (Somnoplasty®) in the Treatment of Habitual Snoring: Results of a European Multicenter Trial", *Acta Otolaryngol*, vol. 120, pp. 981-985 (2000).

Brietzke, S. et al., "Injection snoreplasty: How to treat snoring without all the pain and expense", *Otolaryngology-Head and Neck Surgery*, pp. 503-510 (May 2001).

Cole, P. et al., Review Article "Snoring: A Review and a Reassessment", *The Journal of Otolaryngology*, vol. 24, No. 5, pp. 303-306 (1995).

Coleman, S. et al., "Midline radiofrequency tissue reduction of the palate for bothersome snoring and sleep-disordered breathing: A clinical trial", *Otolaryngology Head and Neck Surgery*, vol. 122, No. 3, pp. 387-394 (Mar. 2000).

Collard, P. et al., "Why Should We Enlarge the Pharynx in Obstructive Sleep Apnea?", *Sleep*, vol. 19, No. 9, pp. S85-S87 (1996).

Courey, M. et al., "Histologic and Physiologic Effects of Electrocautery, $CO_2$ Laser, and Radiofrequency Injury in the Porcine Soft Palate", *Laryngoscope*, vol. 109, pp. 1316-1319 (Aug. 1999).

Dalmasso, F. et al., "Snoring: analysis, measurement, clinical implications and applications", *European Respiratory Journal*, vol. 9, pp. 146-159 (1996).

Dreher, A. et al., "Nasenatmungsbehinderung und schlafbezogene Atmungsstorungen", *Laryngo-Rhino-Otol*, vol. 78, pp. 313-317 (1999).

Ellis, P. et al., "Surgical relief of snoring due to palatal flutter: a preliminary report", *Annals of the Royal College of Surgeons of England*, vol. 75, pp. 286-290 (1993).

Fischer, Y. et al., "Die Radiofrequenzablation des weichen Gaumens (Somnoplastik)", *HNO*, vol. 1, pp. 33-40 (2000).

Gillette, P. et al., "Pediatric Cardiac Pacing", *Cardiology Clinics*, vol. 10, No. 4, pp. 749-754 (Nov. 1992).

Harries, P. et al., "Review Article The surgical treatment of snoring", *Journal of Laryngology and Otology*, vol. 110, pp. 1105-1106 (Dec. 1996).

Huang, L., "Flutter of Cantilevered Plates in Axial Flow", *Journal of Fluids and Structures*, vol. 9, pp. 127-147 (1995).

Huang, L. et al., "Biomechanics of snoring", 5 pages, (Source Unknown) (Date Unknown).

Hukins, C. et al., "Radiofrequency Tissue Volume Reduction of the Soft Palate in Simple Snoring", *Arch Otolaryngol Head Neck Surgery*, vol. 126, pp. 602-606 (May 2000).

Li, K. et al., "Radiofrequency volumetric reduction of the palate: An extended follow-up study", *Otolaryngology Head and Neck Surgery*, vol. 122, No. 3, pp. 410-414 (Mar. 2000).

LaFrentz et al., "Palatal Stiffening Techniques for Snoring in a Novel Canine Model", *Abstracts of the Twenty-Second Annual Mid Winter Research Meeting of the Association for Research in Otolaryngology*, Abstract No. 499, vol. 22, pp. 125-126 (Feb. 13-18, 1999).

Lemperle, G. et al., "PMMA Microspheres (Artecoll) for Skin and Soft-Tissue Augmentation. Part II: Clinical Investigations", *Plastic and Reconstructive Surgery*, vol. 96, No. 3, pp. 627-634 (Sep. 1995).

Littlefield, P. et al., "Snoring surgery: Which is best for you?", *ENT-Ear, Nose, & Throat Journal*, vol. 78, No. 11, pp. 861-870 (Nov. 1999).

Lorenz, C., "If he snores—what can you do about it?", *Today's Woman*, 2 pgs, (Jul. 1948).

Mair, E. et al., "Cautery-assisted palatal stiffening operation", *Otolaryngology Head and Neck surgery*, vol. 122, No. 4, pp. 547-555 (Apr. 2000).

Nutrition for Life International Brochure, "Snoreless™—A Natural Lubricant That Really Works!", 2 pages (Dec. 1999).

Our Health News Brochure, "Snore-Free Nights Guaranteed!", 2 pages (Date Unknown).

Phillips, M., "Stenting therapy for stenosing airway diseases", *Respirology*, vol. 3, pp. 215-219 (1998).

Schwab, R. et al., "Dynamic upper airway imaging during awake respiration in normal subjects and patients with sleep disordered breathing", *Am Rev Respir Dis*, vol. 148, pp. 1385-1398 (1993).

Schwab, R., "Upper Airway Imaging", *Clinics in Chest Medicine*, vol. 19, No. 1, pp. 33-54 (Mar. 1998).

Schwab, R. et al., "Upper airway and soft tissue anatomy in normal subjects and patients with sleep-disordered breathing", *Am Journal of Respir Crit Care Med*, vol. 152, pp. 1673-1689 (1995).

Schwartz, R. et al., "Effects of electrical stimulation to the soft palate on snoring and obstructive sleep apnea", *Journal of Prosthetic Dentistry,* vol. 76, No. 3, pp. 273-281 (Sep. 1996).

Schwartz, A., "Pharyngeal Airway Obstruction in Obstructive Sleep Apnea", *Otolaryngologic Clinics of North America,* vol. 31, No. 6, pp. 911-918 (Dec. 1998).

Sher, A. et al., "The Efficacy of Surgical Modifications of the Upper Airway in Adults With Obstructive Sleep Apnea Syndrome", *Sleep,* vol. 19, No. 2, pp. 156-177 (1996).

Somnoplasty Brochure, "Haven't you suffered from snoring long enough", 2 pages (Date Unknown).

SNAP Brochure, "Our Siagnostic Procedures are a Snap!", *Snap Laboratories Glenview, IL,* 4 pages (Date Unknown).

Stauffer, J. et al., "Pharyngeal Size and Resistance in Obstructive Sleep Apnea", *Amer Rev of Respir Disease,* vol. 136, No. 3, pp. 622-627 (Sep. 1987).

Wheatley, J. et al., "Mechanical properties of the upper airway", *Pulmonary Med,* vol. 4, pp. 363-369 (1998).

Wiltfang, J. et al., "First results on daytime submandibular electrostimulation of suprahyoidal muscles to prevent nighttime hypopharyngeal collapse in obstructive sleep apnea syndrome"; *Intl Journ of Oral & Maxillofacial Surgery,* vol. 28, pp. 21-25 (1999).

Winter, W. et al., "Enlargement of the lateral pharyngeal fat pad space in pigs increases upper airway resistance", *Amer Physiological Society,* pp. 726-731 (1995).

Blumen et al., Radiofrequency Ablation for the Treatment of Mild to Moderate Obstructive Sleep Apnea, Nov., 2002; pp. 2086-2092.

\* cited by examiner

STIFFENING PHARYNGEAL WALL TREATMENT

CROSS-REFERENCE TO RELATED APPLICATION

The present application in a continuation-in-part of commonly assigned and co-pending U.S. patent application Ser. No. 10/066,967 filed Feb. 4, 2002.

BACKGROUND

1. Field of the Invention

This invention is directed to methods and apparatuses for treating the pharyngeal wall of a patient. More particularly, this invention pertains to method and apparatus for treating a pharyngeal wall area as part of a sleep apnea treatment.

2. Description of the Prior Art

Sleep apnea and snoring are complex phenomena. Commonly assigned U.S. Pat. No. 6,250,307 describes various prior techniques and discloses a novel treatment for such conditions (including a permanent palatal implant).

These prior art teachings include Huang, et al., "Biomechanics of Snoring", *Endeavour*, p. 96–100, Vol. 19, No. 3 (1995). That publication estimates that up to 20% of the adult population snores habitually. Snoring can be a serious cause of marital discord. In addition, snoring can present a serious health risk to the snorer. In 10% of habitual snorers, collapse of the airway during sleep can lead to obstructive sleep apnea syndrome. Id. In addition to describing a model for palatal flutter, that publication also describes a model for collapse of the pharyngeal wall.

Notwithstanding efforts have been made to treat snoring and sleep apnea. These include palatal treatments such as electrical stimulation of the soft palate. See, e.g., Schwartz, et al., "Effects of electrical stimulation to the soft palate on snoring and obstructive sleep apnea", *J. Prosthetic Dentistry*, pp. 273–281 (1996). Devices to apply such stimulation are described in U.S. Pat. Nos. 5,284,161 and 5,792,067. Such devices are appliances requiring patient adherence to a regimen of use as well as subjecting the patient to discomfort during sleep. Electrical stimulation to treat sleep apnea is discussed in Wiltfang, et al., "First results on daytime submandibular electrostimulation of suprahyoidal muscles to prevent night-time hypopharyngeal collapse in obstructive sleep apnea syndrome", *International Journal of Oral & Maxillofacial Surgery*, pp. 21–25 (1999).

Surgical treatments for the soft palate have also been employed. One such treatment is uvulopalatopharyngoplasty (UPPP) where about 2 cm of the trailing edge of the soft palate is removed to reduce the soft palate's ability to flutter between the tongue and the pharyngeal wall of the throat. See, Huang, et al., supra at 99 and Harries, et al., "The Surgical treatment of snoring", *Journal of Laryngology and Otology*, pp. 1105–1106 (1996) which describes removal of up to 1.5 cm of the soft palate. Assessment of snoring treatment is discussed in Cole, et al., "Snoring: A review and a Reassessment", *Journal of Otolaryngology*, pp. 303–306 (1995). Huang, et al., propose an alternative to UPPP which proposal includes using a surgical laser to create scar tissue on the surface of the soft palate. The scar is to reduce flexibility of the soft palate to reduce palatal flutter. RF ablation (so-called Somnoplasty as advocated by Somnus Technologies) is also suggested to treat the soft palate. RF ablation has also been suggested for ablation of the tongue base.

In pharyngeal snoring and sleep apnea, the pharyngeal airway collapses in an area between the soft palate and the larynx. One technique for treating airway collapse is continuous positive airway pressure (CPAP). In CPAP air is passed under pressure to maintain a patent airway. However, such equipment is bulky, expensive and generally restricted to patients with obstructive sleep apnea severe enough to threaten general health. Huang, et al. at p. 97.

Treatments of the pharyngeal wall include electrical stimulation is suggested in U.S. Pat. No. 6,240,316 to Richmond et al. issued May 29, 2001, U.S. Pat. No. 4,830,008 to Meer issued May 16, 1989, U.S. Pat. No. 5,158,080 to Kallok issued Oct. 27, 1992, U.S. Pat. No. 5,591,216 to Testerman et al. issued Jan. 7, 1997 and PCT International Publication No. WO 01/23039 published Apr. 5, 2001 (on PCT International Application No. PCT/US00/26616 filed Sep. 28, 2000 with priority to U.S. Ser. No. 09/409,018 filed Sep. 29, 1999). U.S. Pat. No. 5,979,456 to Magovern dated Nov. 9, 1999 teaches an apparatus for modifying the shape of a pharynx. These teachings include a shape-memory structure having an activated shape and a quiescent shape. Dreher et al., "Influence of nasal obstruction on sleep-associated breathing disorders", So. Laryngo-Rhino-Otologie, pp. 313–317 (June 1999), suggests using nasal stents to treat sleep associated breathing disorders involving nasal obstruction. Upper airway dilating drug treatment is suggested in Aboubakr, et al., "Long-term facilitation in obstructive sleep apnea patients during NREM sleep", J. Applied Physiology, pp. 2751–2757 (December 2001).

Surgical treatments for sleep apnea are described in Sher et al., "The Efficacy of Surgical Modifications of the Upper Airway in Adults with Obstructive Sleep Apnea Syndrome", *Sleep*, Vol. 19, No. 2, pp. 156–177 (1996). Anatomical evaluation of patients with sleep apnea or other sleep disordered breathing are described in Schwab, et al., "Upper Airway and Soft Tissue Anatomy in Normal Subjects and Patients with Sleep-Disordered Breathing", *Am. J. Respir. Crit. Care Med.*, Vol. 152, pp. 1673–1689 (1995) ("Schwab I") and Schwab et al., "Dynamic Upper Airway Imaging During Awake Respiration in Normal Subjects and Patients with Sleep Disordered Breathing", *Am. Rev. Respir. Dis.*, Vol. 148, pp. 1385–1400 (1993) ("Schwab II). In Schwab I, it is noted that apneic patients have a smaller airway size and width and a thicker lateral pharyngeal wall. For reviews of pharyngeal wall thickness and other structure and obstructive sleep apnea, see, also, Wheatley, et al., "Mechanical Properties of the Upper Airway", Current Opinion in Pulmonary Medicine, pp. 363–369 (November 1998); Schwartz et al., "Pharyngeal airway obstruction in obstructive sleep apnea: pathophysiology and clinical implication", Otolaryngologic Clinics of N. Amer., pp. 911–918 (December 1998); Collard, et al., "Why should we enlarge the pharynx in obstructive sleep apnea?", Sleep, (9 Suppl.) pp. S85–S87 (November 1996); Winter, et al., "Enlargement of the lateral pharyngeal fat pad space in pigs increases upper airway resistance", J. Applied Physiology, pp. 726–731 (September 1995); and Stauffer, et al., "Pharyngeal Size and Resistance in Obstructive Sleep Apnea", Amer. Review of Respiratory Disease, pp. 623–627 (September 1987).

There are contrasting opinions in the medical literature on the mechanisms of OSA. OSA patients are a heterogeneous group; there are differing locations and patterns of pharyngeal collapse for each person. In addition to the physical findings and properties which characterize the pharynx in patients with OSA such as increased collapsibility, increased compliance, increased resistance, and decreased cross-sectional area, the physical properties and spatial relationships of the pharyngeal airway, head, and neck, as well as the neuromuscular integrity of the airway (reflexes affecting upper airway caliber) and mechanisms of breathing control (pharyngeal inspiratory muscle function) must also be considered relevant in their contribution to the mechanism and precipitation of upper airway collapse. Hudgel D W, *Mechanisms of Obstructive Sleep Apnea*. Chest 1992; 101:541–49. Fairbanks DNF, Fujita S, Snoring and Obstructive Sleep Apnea. Raven Press Ltd., New York, 1994.

In general, obstructive apnea occurs during sleep, when the pharyngeal dilator muscle activity (genioglossus, tensor palatini, geniohyoid, stylohyoid) that normally maintains airway patency during inspiration through dilation of the airway, is diminished. (Fairbanks DNF, Fujita S, Snoring and Obstructive Sleep Apnea. Raven Press Ltd., New York, 1994.2, p. 85). When the intraluminal negative pressure of the airway reaches a critical point, the combination of redundant tissues and the loss of pharyngeal muscle tone causes airway collapse during inspiration. Please note, obstruction has been shown to occur during expiration and inspiration (Schwab R J et al., *Dynamic imaging of the upper airway during respiration in normal subjects*. J Appl Physiol 1993; 74(4):1504–1514. Schwab R J, *Functional Properties of the Pharyngeal Airway*. Sleep 1996; 19(10):S170–S174. 8, 9); details on how upper airway area changes during the respiratory cycle can be found in the cited literature. Surgical treatments are aimed at eliminating any collapsible tissue in the airway and reducing airway resistance without creating functional impairment of the upper airway structures.

SUMMARY OF THE INVENTION

According to one aspect of the present invention, methods and apparatuses are disclosed for treating a pharyngeal airway having a pharyngeal wall of a patient at least partially surrounding and defining said airway. The method includes selecting an implant dimensioned so as to be implanted beneath a mucosal layer of the pharyngeal wall and extending transverse to said wall. The implant has mechanical characteristics for the implant, at least in combination with a fibrotic tissue response induced by the implant, to stiffen aid pharyngeal wall to resist radial collapse. The implant is implanted into the pharyngeal wall transverse to a longitudinal axis of the airway.

DESCRIPTION OF THE PREFERRED EMBODIMENT

A. Physiology Background

Referring now to the several drawing figures, in which identical elements are numbered identically throughout, a description of a preferred embodiment of the present invention will now be provided.

The disclosures of U.S. Pat. No. 6,250,307 and PCT International Publications No. WO 01/19301 (PCT/US00/40830) and WO 02/13738 (PCT/US01/24255) are incorporated herein by reference.

Figure 1:
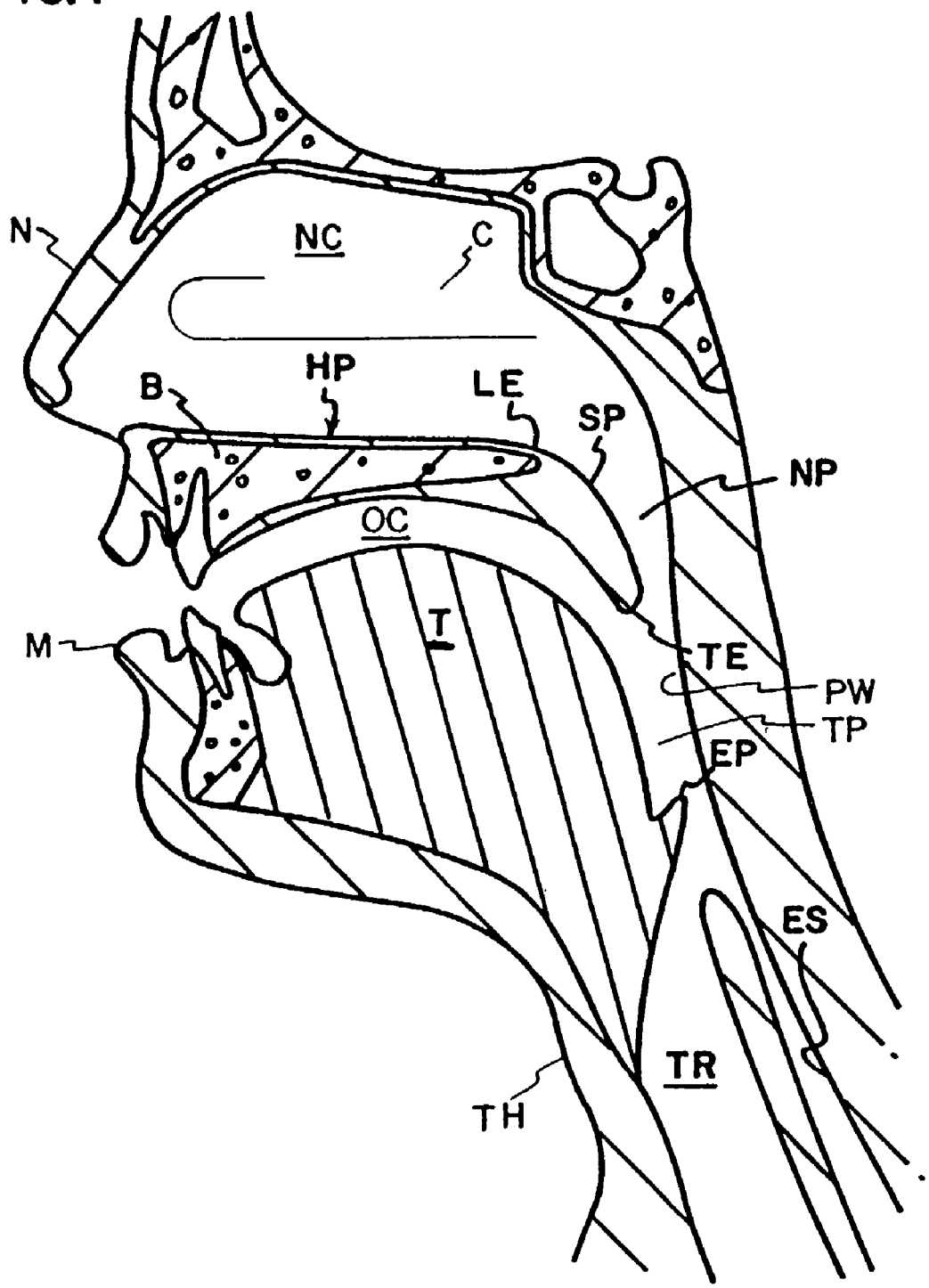
FIG. 1 shows, in cross-section, a naso-pharyngeal area of an untreated patient.

FIG. 1 shows, in cross-section, a naso-pharyngeal area of an untreated patient. FIG. 1 shows the nose N, mouth M and throat TH. The tongue T is shown in an oral cavity OC of the mouth. A hard palate HP (containing a bone B) separates the oral cavity OC from the nasal cavity NC. The nasal concha C (soft tissue which defines, in part, the nasal sinus—not shown) resides in the nasal cavity NC.

The soft palate SP (a muscle activated soft tissue not supported by bone) depends in cantilevered manner at a leading end LE from the hard palate HP and terminates at a trailing end TE. Below the soft palate SP, the pharyngeal wall PW defines the throat passage TP. A nasal passage NP connects the nasal cavity NC to the pharyngeal wall PW. Below an epiglottis EP, the throat passage TP divides into a trachea TR for passing air to the lungs and an esophagus ES for passing food and drink to the stomach.

The soft palate SP is operated by muscles (not separately shown and labeled) to lift the soft palate SP to urge the trailing edge TE against the rear area of the pharyngeal wall PW. This seals the nasal cavity NC from the oral cavity OC during swallowing. The epiglottis EP closes the trachea TR during swallowing and drinking and opens for breathing.

For purposes of this disclosure, the nasal cavity NC, oral cavity OC and throat passage TP are collectively referred to as the naso-pharyngeal area of the patient (defining, in part, the pharyngeal airway PA in FIGS. 5 and 7) with the area including the various body surfaces which cooperate to define the nasal cavity NC, oral cavity OC and throat passage TP. These body surfaces include outer surfaces of the nasal concha C, the upper and lower surfaces of the soft palate SP and outer surfaces of the pharyngeal wall PW. Outer surfaces means surfaces exposed to air. Both the upper and lower surfaces of the soft palate SP are outer surfaces.

Snoring can result from vibration of any one of a number of surfaces or structures of the naso-pharyngeal area. Most commonly, snoring is attributable to vibration of the soft palate SP. However, vibratory action of the nasal concha C and the pharyngeal wall PW can also contribute to snoring sounds. It is not uncommon for vibratory action from more than one region of the naso-pharyngeal area to contribute to snoring sounds. Sleep apnea can result from partial or full collapse of the nasopharyngeal wall during sleep.

Figure 5:
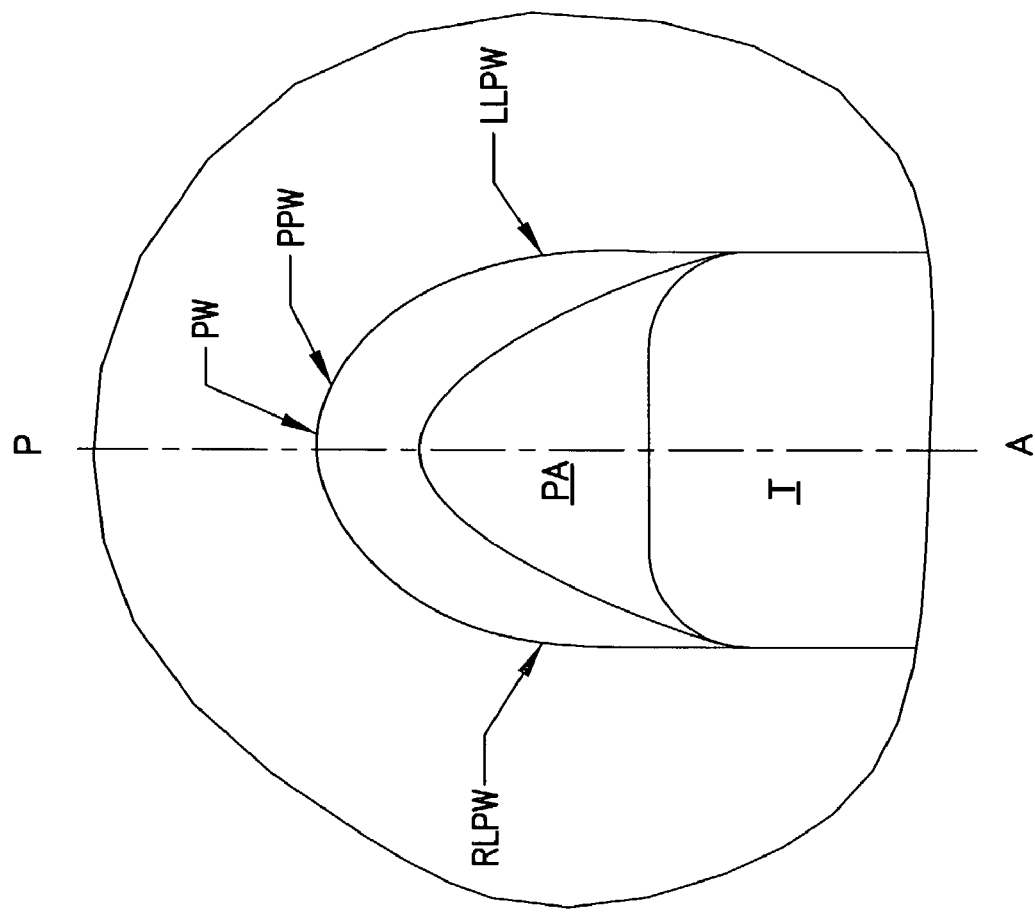
FIG. 5 is a schematic cross-sectional view (taken generally along line 5—5 in FIG. 1) of a pharyngeal airway at a position in a person with the airway defined by opposing portions of a pharyngeal wall and a base of a tongue.

FIG. 5 shows a schematic representation of a cross-section of a throat with the pharyngeal airway PA defined by the pharyngeal wall PW and the tongue T. The anterior-posterior axis is labeled A-P to assist in discerning the orientation. The pharyngeal wall PW is shown as including the left lateral pharyngeal wall LLPW, right lateral pharyngeal wall RLPW and posterior pharyngeal wall PPW.

B. Disclosure of Commonly Assigned Applications

Figure 2:
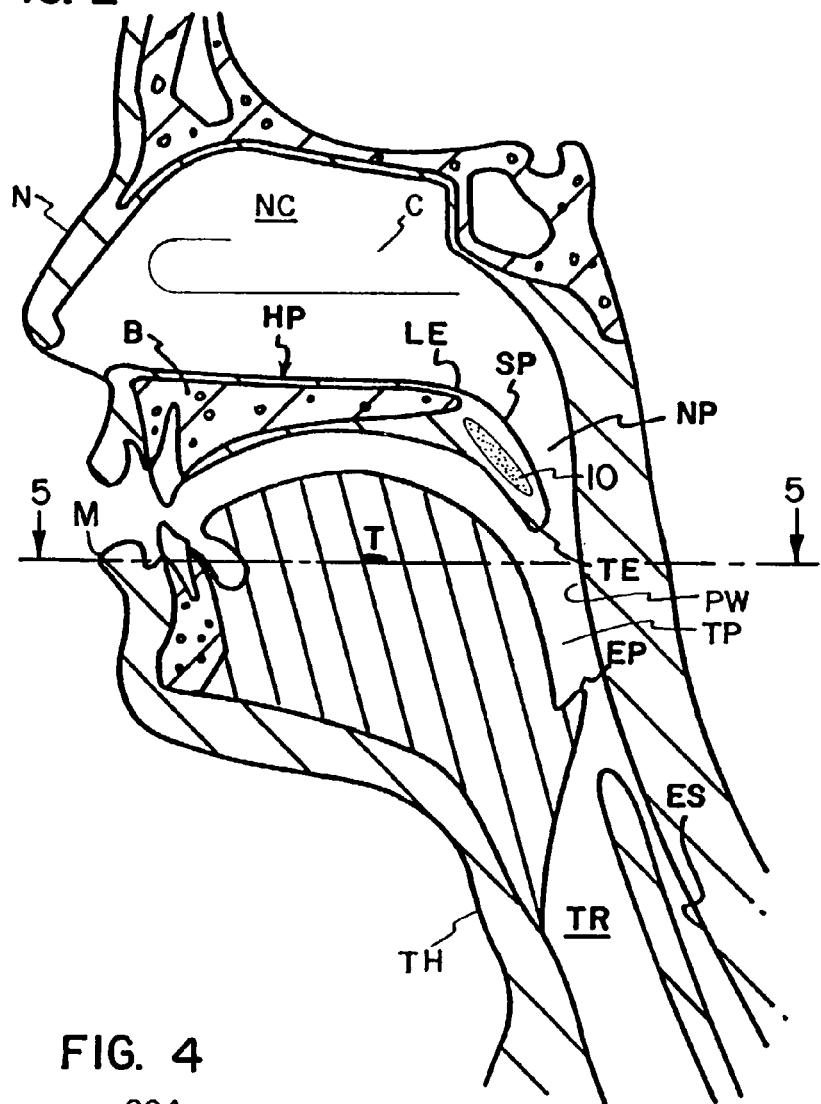
FIG. 2 is the view of FIG. 1 with the soft palate containing an implant in the form of a bolus of micro-beads deposited in a linear path.
Figure 3:
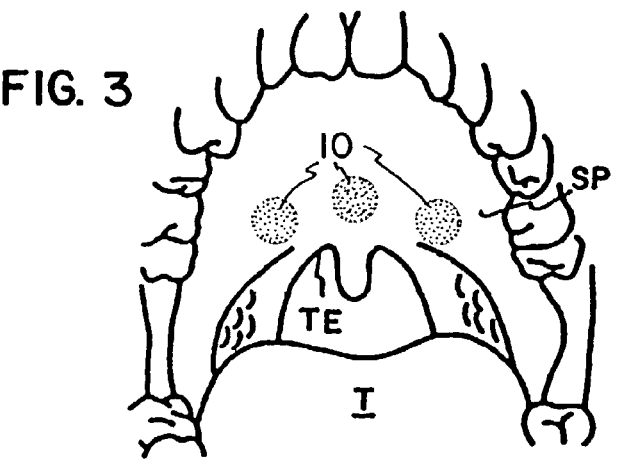
FIG. 3 is a frontal view of the patient of FIG. 3 showing an alternative embodiment with micro-beads deposited as spherical deposits.

In addition to disclosing the teachings of U.S. Pat. No. 6,250,307 and the teachings of selected embodiments of PCT International Publication Nos. WO 01/19301 (both incorporated herein by reference), commonly assigned and co-pending PCT International Publication No. WO 02/13738 (incorporated by reference) describes techniques for stiffening tissue of the pharyngeal airway with a bolus of particulate matter. FIGS. 2 and 3 show are taken from International Publication No. WO 02/13738 and show an implant 10 as a bolus of particulate matter. An example of such particulate matter would be micro-beads. An example of such is taught in U.S. Pat. Nos. 5,792,478 and 5,421,406. These patents teach carbon-coated metallic or ceramic particles having cross-sectional dimensions of between 100 and 1,000 microns. The particles are carried in a fluid or gel. These patents state that upon insertion into body tissue, the particles do not migrate significantly and, apparently due to fibrotic response, the tissue into which the particles are injected stiffens.

The particles of U.S. Pat. Nos. 5,792,478 and 5,421,406 are one example of particles for stiffening injection. Such particles can also include ceramic particles or pure carbon or other bio-compatible particles. The particles can be carried in a liquid or gel medium. The particles can have multi-modal particle size distributions (i.e., a mix of two or more sizes of particles with the smaller particles filling interstitial spaces between larger particles).

The bolus 10 of particles can be applied by a needle to inject the bolus 10 into the soft palate SP. The bolus can be the same volume as the volume of the implants 20 of FIGS. 8 and 9 of U.S. Pat. No. 6,250,307. With reference to FIG. 3, a multiple of bolus injections can be made in the soft palate resulting in deposition of generally spherical deposits 10' of particles. Alternatively, an injecting needle can be withdrawn while simultaneously ejecting particles for the bolus 10 (FIG. 2) to be deposited in a line similar in dimensions to the implants 20 of FIGS. 8 and 9 of U.S. Pat. No. 6,250,307.

The foregoing emphasizes the use of implants to stiffen the soft palate SP. Implants 10 can be placed in any of the tissue of the naso-pharyngeal area (e.g., the concha C, soft palate SP or pharyngeal wall PW) to treat snoring. Also, such a treatment can stiffen the tissue of the throat and treat sleep apnea resulting from airway collapse by stiffening the airway.

Figure 4:
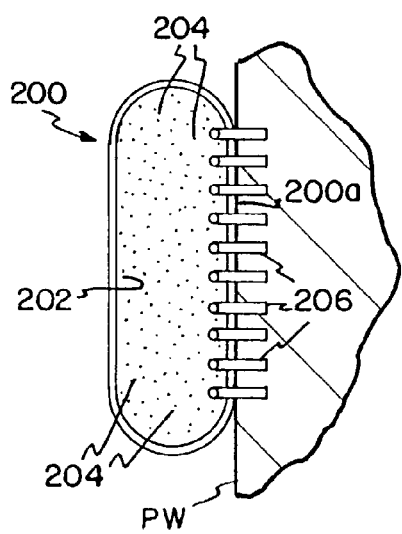
FIG. 4 is a schematic representation showing a patch for delivering a bolus of micro-beads through a plurality of needles.

While a needle deposition of a bolus of particles may be preferred, the bolus can be applied in other manners. FIG. 4 illustrates deposition of particulates through a patch 200 having a volume 202 containing such micro-beads 204.

One side 200a of the patch 200 contains an array of micro-needles 206 communicating with the volume 202. The needles 206 may be small diameter, shallow penetration needles to minimize pain and blood. Examples of shallow, small diameter needles are shown in U.S. Pat. No. 5,582,184 to Erickson et al. Placing the surface 200a against the tissue (e.g., the pharyngeal wall PW as shown in FIG. 4), the needles 206 penetrate the outer surface of the tissue PW. The patch 200 can then be compressed (by finger pressure, roller or the like) to eject the beads 204 from the volume 200 through the plurality of needles 206. The patch 200 can be provided with interior dividing walls (not shown) so that some of the volume of beads 204 is ejected through each needle 206. The side 200a acts as a stop surface to ensure control over the penetration depth of the needles 206 to reduce risk of undesired puncture of underlying structures.

Stiffening of the naso-pharyngeal tissue provides structure to reduce vibration and snoring. Such structure reduces airway collapse as a treatment for sleep apnea. Commonly assigned and co-pending U.S. patent application Ser. No. 10/066,967 filed Feb. 4, 2002 teaches stiffening of the pharyngeal wall with other stiffening techniques including pre-compressing the wall and stiffening the wall in a compressed state.

C. Transverse Stiffening Implant

Figure 6:
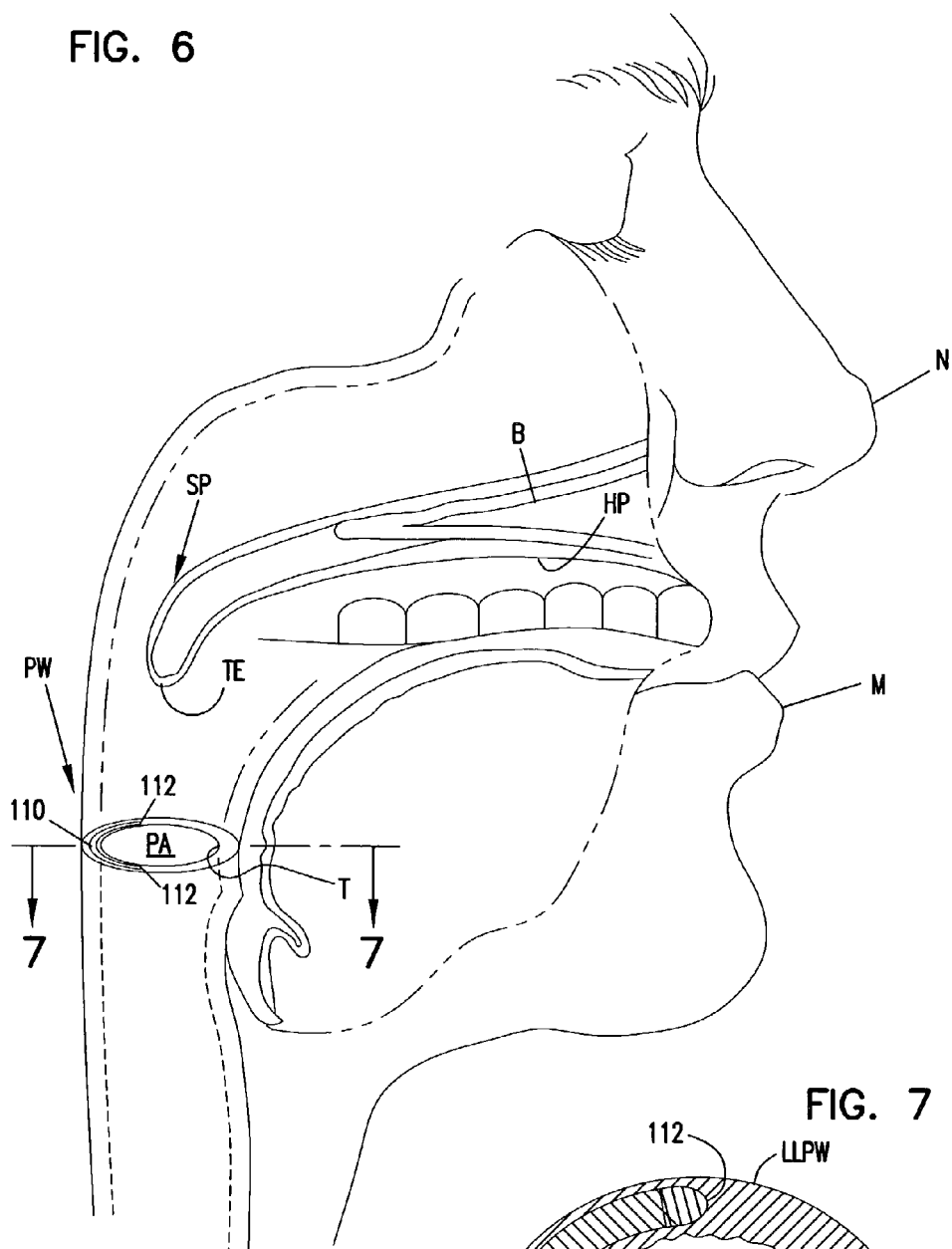
FIG. 6 is a view similar to that of FIG. 1 (only showing patient's right side) with a device according to the present invention placed in the pharyngeal wall and with the pharyngeal wall and the device shown in perspective for ease of illustration.
Figure 7:
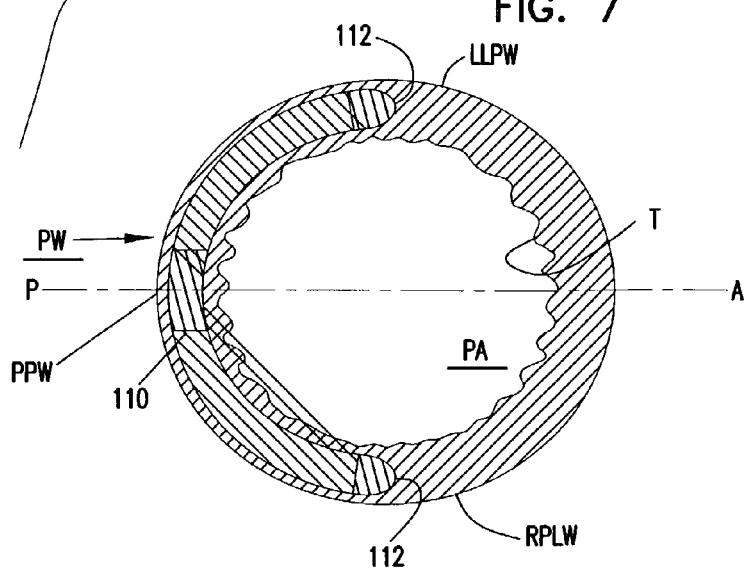
FIG. 7 is a cross-sectional view taken along section line 7—7 of FIG. 6.
Figure 8:
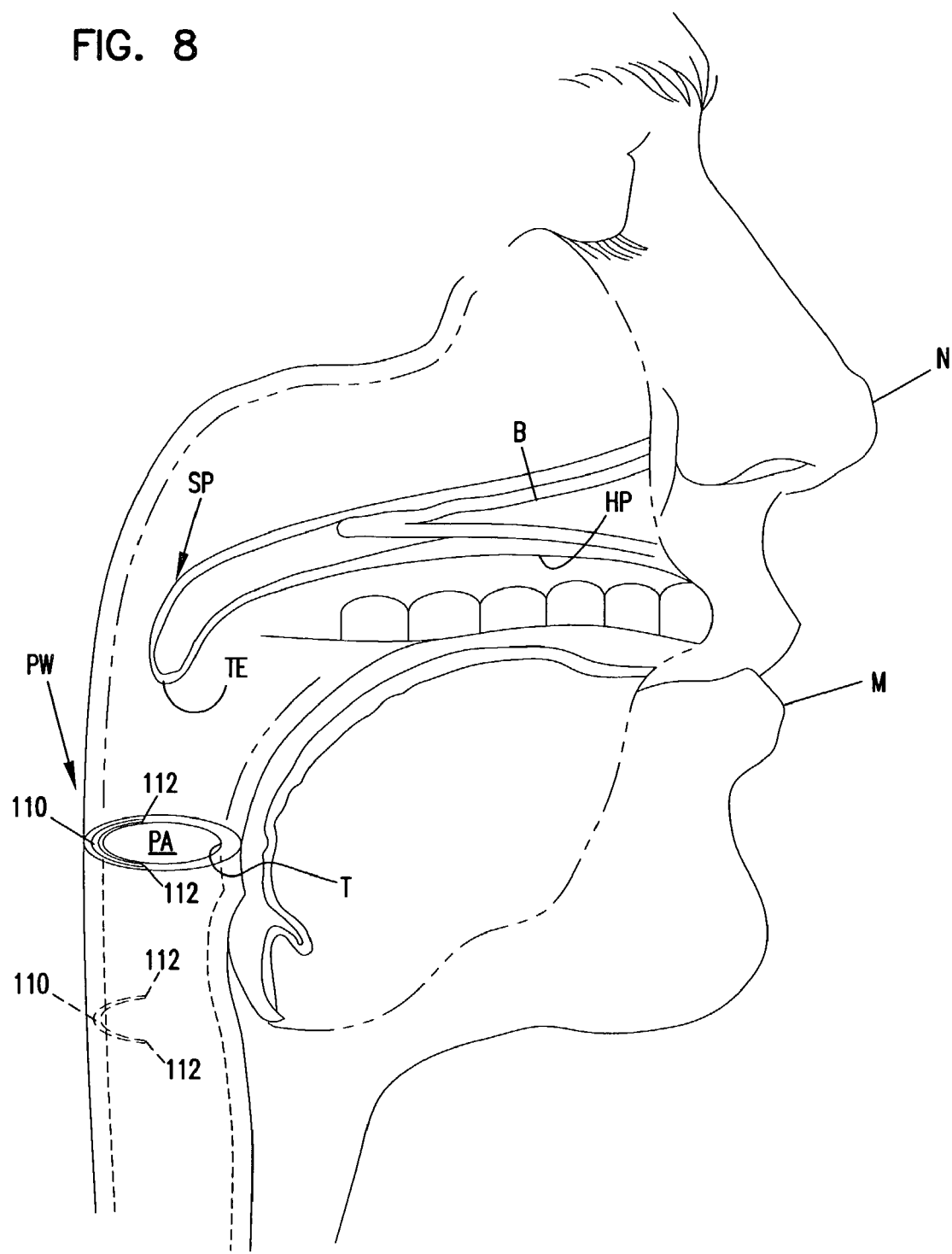
FIG. 8 is a view similar to that of FIG. 6 showing multiple devices placed in the pharyngeal wall.

FIGS. 6–7 illustrate the device of the present invention in a pharyngeal wall. As will be further discussed, the implant can be placed at any location along the length of the airway to stiffen the posterior and lateral walls of the pharyngeal wall. While only one implant is shown in FIGS. 6–7, multiple implants 100 can be placed in the pharyngeal wall as shown in FIG. 8.

The device is an implant 110 of biocompatible material selected to induce a fibrotic tissue response. A preferred device is a flexible braid 110 of polyester fibers. In a preferred design, the implant 110 has a diameter of about 2 mm. A length of 10 mm to 20 mm (depending on patient) can cover about 180 degrees surrounding the pharyngeal airway PA. In one embodiment, the implant is elastic so as to be biased toward an at rest position following bending the implant along its longitudinal axis.

The braided implant 110 is preferably formed of a plurality of fibers of similar material (i.e., all polyester fibers). The fibers are bonded together near the ends 112 of the braid to prevent excessive fraying.

The braid 110 may be a simple braid (such as that shown in International Publication No. WO 01/19301 A1 (PCT/US00/40830)) or may be any other braid geometry such as so-called three dimensional braids as described in Du et al., "Geometric Modeling of 3-D Braided Preforms For Composites", Proceedings of $5^{th}$ Textile Structural Composites Symposium, Drexel University, Philadelphia, Pa. (1991) and Ko et al., "Braiding", Engineering Materials Handbook, Vol. 1, Composites, Reinhart, T. J. Editor, ASM International, Metal Park, Ohio pp. 519–528 (1988). An example of such a more complex braid is shown in commonly assigned and co-pending U.S. patent application Ser. No. 09/814,471 filed Mar. 21, 2001 and filed internationally as PCT/US02/07966 on Mar. 14, 2002, that is hereby incorporated by reference in its entirety.

According to the '471 application, such a 3-D braid could be a 1×1 3-D braid formed on a 24-carrier machine with a braiding angle of 45 degrees and a braid diameter of about 2 mm. The braid is formed of 24 braider yarns of 70 denier yarns with 2 denier/fil (air-textured yarns may be substituted as discussed below). The braid can be formed with 8 axial polyester yarns of 400 denier (7.9–8 mil) monofilament. While a core-less braid is preferred, cores can be added for stiffness. Such cores may be 10 monofilaments of polyester at 400 denier per filament. It will be appreciated that 3-D braid construction as described form no part of this invention per se and may be formed as described in the aforementioned articles.

In a preferred embodiment of a braid as disclosed in the '471 application, the fibers are heat bonded together (e.g., by application of ultrasonic energy) at two locations spaced 1 mm from the ends of the braid. The ends then be frayed for the individual fibers to splay freely from the bonded locations at the ends. The bonded locations insure the fraying does not migrate throughout the entire length of the braid. As an alternative to fraying, the ends may be left braided but unbonded. The ends are then free to fray with the bonded locations insuring any such fraying does not migrate.

With the structure of a braid as disclosed in the '471 application and as described above, the frayed ends present a softened tip to tissue as compared to un-frayed ends of an otherwise identical braid. The softened frayed ends reduce likelihood of migration of the braid in the tissue of the soft palate.

The fibers of the braid may be air textured yarns so that the braid presents a plurality of fiber loops along its length. These loops present increased volume of interstitial space in the braid for increased tissue growth to further reduce the probability of migration of the braid in tissue. Not all of the fibers need be air-textured yarns. For example, 50% (or some different percentage) of the fibers can be un-textured (or straight) polyester fibers (or silk or other material) and the remaining 50% can be air-textured polyester fibers (or silk or other material). This ratio can be changed at a braid designer's convenience. Also, as an alternative embodiment, in the braid, air-textured fibers can be placed predominantly in the interior of the braid for a less stiff braid and more interior interstitial space for tissue in-growth.

The implant 110 is placed in the pharyngeal wall PW with the longitudinal axis of the braid 110 bending in the wall PW and extending transverse to the anterior-posterior axis A-P of the airway PA and also transverse relative to a longitudinal axis of the airway PA. The device 110 thus positioned wraps at least partially around the airway PW to reside in the posterior and lateral pharyngeal walls PPW, RLPW, LLPW.

Preferably, the implant is placed in or beneath a mucosal layer. The device can have a radiopaque marker 111 to assist in visualization of the implant during and after placement. With such marker, the device's position and influence on swallowing can be assessed, the device's effect on maintaining the airway patent at various inspiratory pressures can be visualized. The marker and implant should be magnetic resonance imaging (MRI) compatible.

The location of pharyngeal collapse in a patient is identified so that the device can be targeted for the most appropriate location in the pharynx. The majority of airway collapse is believed to occur in the retropalatal region because the airway narrowing has been shown to be greatest in the retropalatal region. Schwab R J, *Upper Airway Imaging*. Clinics in Chest Medicine 1998; 19(1):33–54. This region is defined as the region from the level of the hard palate to the caudal tip of the soft palate (uvula). However, studies have also shown that collapse also occurs in the retroglossal region, defined from the caudal margin of the soft palate to the base of the epiglottis. See, e.g., Hudgel D W, *Mechanisms of Obstructive Sleep Apnea*. Chest 1992; 101:541–49.

A body of literature indicates that the lateral pharyngeal walls, rather than the anterior-posterior walls of the pharynx, are the structures which mediate the changes in upper airway size in OSA. Schwab R J, *Upper Airway Imaging*. Clinics in Chest Medicine 1998; 19(1):33–54; Trudo F J et al., *State-related Changes in Upper Airway Caliber and Surrounding Soft-Tissue Structures in Normal Subjects*. Am J Respir Crit Care Med 1998; 158:1259–1270; Schwab R J, *Functional Properties of the Pharyngeal Airway*. Sleep 1996; 19(10): S170–S174; Schwab R J et al., *Upper Airway and Soft Tissue Anatomy in Normal Subjects and Patients with Sleep-Disordered Breathing*. Am J Respir Crit Care Med 1995; 152:1673–1689. Müller's maneuver with fiberoptic nasopharyngoscopy and cephalometric measurement are presently the key diagnostic tools used to identify the location of airway narrowing causing an apneic episode. See, Fairbanks DNF, Fujita S, Snoring and Obstructive Sleep Apnea. Raven Press Ltd., New York, 1994, p. 92. Fiberoptic endoscopy with or without the Muller maneuver has been shown to be able to effectively define the pattern and location of pharyngeal collapse in children. Fairbanks, supra, Ref. No. 42, p. 29. However, contrasting literature claims that the Muller maneuver has not been demonstrated to accurately simulate an apneic event during sleep (Schwab R J, *Upper Airway Imaging*. Clinics in Chest Medicine 1998; 19(1):33–54) and proposes that a combination of MR imaging and nasopharyngoscopy with a Muller maneuver prior to UPPP may improve outcome after surgery. For example, if the nasopharyngoscopy with Muller maneuver demonstrates retroglossal collapse and the MR imaging demonstrates primarily retroglossal narrowing, surgery directed at advancing the tongue such as geniohyoid advancement or maxillomandibular advancement should be considered rather than UPPP.

Posterior pharyngeal wall movement is observed in swallowing. Jones B, Donner M W, Normal and Abnormal Swallowing. Springer-Verlag, New York, 1991. Schwab has demonstrated that thickening of the lateral pharyngeal muscular walls is the major factor that leads to narrowing of the apneic retropalatal airway. Schwab R J et al., *Upper Airway and Soft Tissue Anatomy in Normal Subjects and Patients with Sleep-Disordered Breathing*. Am J Respir Crit Care Med 1995; 152:1673–1689.

The basis for the increased thickness of the lateral pharyngeal walls in apneics is unknown. Experiments utilizing HUPSEC (Hydrogen Ultrathin Phase-Encoded Spectroscopy) in conjunction with MR imaging indicate that the increased thickness of lateral pharyngeal wall in patients with sleep apnea is not secondary to increased fat infiltration or edema.

Another plausible explanation for the thickening of the lateral walls is that weight gain results in increased muscle mass and an increase in the size of the lateral pharyngeal walls as well as the tongue and soft palate. Therefore, obesity may predispose to sleep apnea by theoretically increasing the size of the upper airway soft-tissue structures rather than by the direct deposition of fat in the parapharyngeal fat pads or by compressing the lateral airway walls by these fat pads. Studies have shown that the parapharyngeal fat pads do not compress the lateral airway walls in apneics. Schwab R J et al., *Upper Airway and Soft Tissue Anatomy in Normal Subjects and Patients with Sleep-Disordered Breathing*. Am J Respir Crit Care Med 1995; 152:1673–1689.

Apneics have thicker lateral pharyngeal walls when they are awake and these structures become even thicker during sleep. Schwab R J, *Functional Properties of the Pharyngeal Airway*. Sleep 1996; 19(10):S170–S174. Studies have demonstrated a decrease in the electromyographic activity of the muscles of the lateral pharyngeal walls during sleep as well as the tensor palatini muscle of the soft palate. Trudo F J et al., *State-related Changes in Upper Airway Caliber and Surrounding Soft-Tissue Structures in Normal Subjects*. Am J Respir Crit Care Med 1998; 158:1259–1270; Wheatley et al, *Influence of Sleep on Response to Negative Airway*

*Pressure of Tensor Palatini Muscle and Retropalatal Airway.* J Appl Physiol 1993; 75(5):2117–2124. The decrease in EMG activity may cause relaxation of these structures, contributing to the lateral wall thickening and airway narrowing. However, thickening of the lateral walls during sleep may be associated with state-related changes (asleep vs. awake) in the conformation of the soft palate and tongue.

A complex three-dimensional biomechanical interaction may exist between the tongue, soft palate and lateral pharyngeal walls. The walls are a complex structure made up of a number of muscles including the hypoglossus, styloglossus, stylohyoid, stylopharyngeus, palatoglossus, palatopharyngeus, the pharyngeal constrictors, lymphoid tissue (palatine tonsils), and pharyngeal mucosa. The biomechanical relationships between these muscles and the way they interact with the soft palate and tongue are not well understood, nor is it understood how the lateral pharyngeal wall moves during respiration or during apnea to modulate airway size.

Whether the airway actually collapses laterally or A-P is not discussed in the literature. MR anatomical studies demonstrate posterior movement and thickening of the soft palate with sleep as well as lateral pharyngeal wall thickening. Trudo F J et al., *State-related Changes in Upper Airway Caliber and Surrounding Soft-Tissue Structures in Normal Subjects.* Am J Respir Crit Care Med 1998; 158: 1259–1270. Other studies have shown that increasing increment levels of effective CPAP therapy results in increased airway volume and area within the retropalatal and retroglossal regions, greater lateral than A-P airway dimensional changes, a decrease in the lateral pharyngeal wall thickness, and an increase in the distance between the lateral pharyngeal fat pads. Schwab R J, *Functional Properties of the Pharyngeal Airway.* Sleep 1996; 19(10):S170–S174. Furthermore, effective mandible repositioning devices have been shown to thin the lateral pharyngeal walls; it is theorized that these devices may put traction on the lateral walls, resulting in the thinning of the walls. Subsequently, designing a device that affects the lateral pharyngeal walls seems appropriate in effectively addressing OSA.

An effective device preferably establishes a pressure differential of 8 cm $H_2O$ between nasal pressure and pharyngeal critical pressure ($P_{crit}$) to eliminate obstructive sleep apnea and snoring. The critical pressure is defined as the pressure that is equal to the pressures exerted on the airway by the surrounding tissue which is equal to the pressures tending to collapse the airway See, Gold A R, Schwartz A R, *The Pharyngeal Critical Pressure.* Chest 1996; 110:1077–88. It is determined by finding the level of nasal pressure below which maximal inspiratory airflow ceases (airway collapse). Schwarz A R et al., *Effect of Uvulopalatopharyngoplasty on Upper Airway Collapsibility in Obstructive Sleep Apnea.* Am Rev Respir Dis 1992; 145(3): 527–532. A higher $P_{crit}$ equates to an increase in collapsibility. The $P_{crit}$ for normal people is <–8 cm $H_2O$. For snorers the $P_{crit}$ is approximately –4 cm $H_2O$, and for those with OSA (obstructive sleep apnea), the $P_{crit}$ is approximately 0 cm $H_2O$. See, Gold A R, supra.

The implant should be able to withstand a pressure of 4.4 cm $H_2O$ to prevent collapse. This was the upper airway suction closing pressure found in OSA patient studies by Issa F Q, Sullivan C E, *Upper Airway Closing Pressures in Obstructive Sleep Apnea.* J Appl Physiol 1984; 57(2):520–527. Studies have shown that by sleeping with one's mouth open, a 4 cm $H_2O$ increase in $P_{crit}$ can occur. See, Gold A R, Schwartz A R, *The Pharyngeal Critical Pressure.* Chest 1996; 110:1077–88. Effective UPPP surgery has demonstrated a reduction in $P_{crit}$ from –0.8 to –7.3 cm $H_2O$. Schwarz A R et al., *Effect of Uvulopalatopharyngoplasty on Upper Airway Collapsibility in Obstructive Sleep Apnea.* Am Rev Respir Dis 1992; 145(3):527–532.

Normal individuals maintain a positive pharyngeal transmural pressure of approximately 0 to 10 mm Hg (13.6 cm $H_2O$) during sleep. In contrast, upper airway obstruction in apneics is associated with development of negative transmural pressure during sleep. Clinically significant levels of obstructive sleep apnea can be produced when a nasal pressure of –10 cm $H_2O$ is applied to normal subjects during sleep. These findings suggest that a disturbance in reflex responses is not necessary for the development of recurrent obstructive apneas (as some literature suggests). Rather, structural or neuromuscular factors that decrease the pharyngeal transmural pressure will predispose to this disorder. King E D, O'Donnell C P, Smith P L, Schwartz A R, *A Model of Obstructive Sleep Apnea in Normal Humans.* Am J Respir Crit Care Med 2000; 161:1979–1984.

The dynamic biomechanical relationships between the upper airway muscles that allow physiologic functions like vocalization, swallowing, and respiration to occur is complex. Schwab R J, *Upper Airway Imaging.* Clinics in Chest Medicine 1998; 19(1):33–54. In the pharyngeal phase of swallowing, more than two dozen muscles are required to function together to effectively transport a bolus from the mouth to the esophagus. The posterior pharyngeal wall movement has been studied by Palmer et al., there is considerable mobility normally present in the posterior pharyngeal wall (retropalatal and retroglossal). Palmer J B et al. *Motions of the Posterior Pharyngeal Wall in Swallowing.* Laryngoscope 1999; 98:414–417.

The implant is sized to be implantable in a typical apneic based upon the following anatomical measurements (Schwab R J et al., *Upper Airway and Soft Tissue Anatomy in Normal Subjects and Patients with Sleep-isordered Breathing.* Am J Respir Crit Care Med 1995; 152:1673–1689):

a. thickness of lateral pharyngeal wall: (approx 30 mm)
b. anterior-posterior diameter of airway: (4.7+/–2.5 mm)
a. lateral diameter of airway (6.7+/–4.5 mm) at the level of the minimum airway area in apneics.

Figure 9:
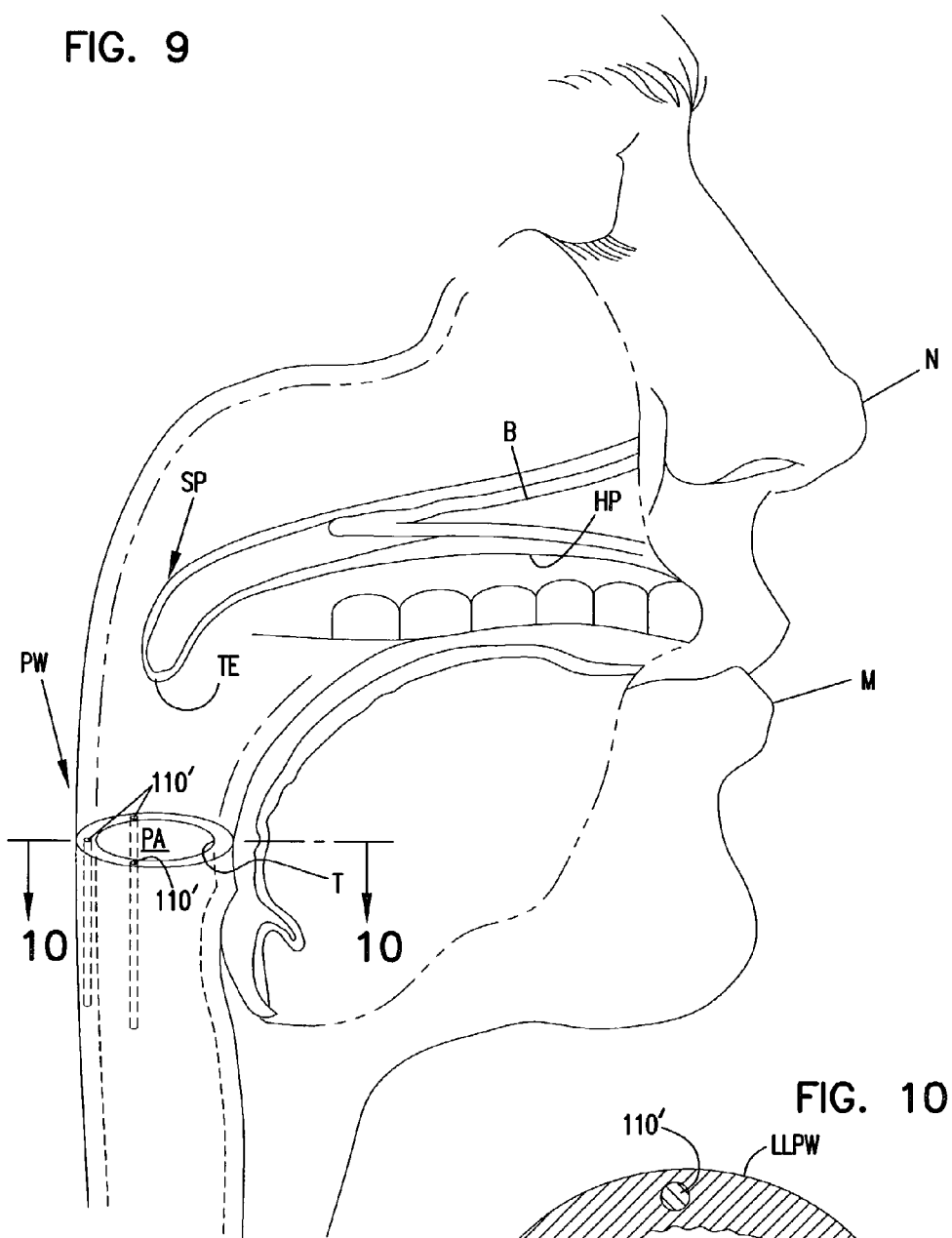
FIG. 9 is a view similar to that of FIG. 6 showing multiple devices placed in the pharyngeal wall and oriented parallel relative to a longitudinal axis of the air passage.
Figure 10:
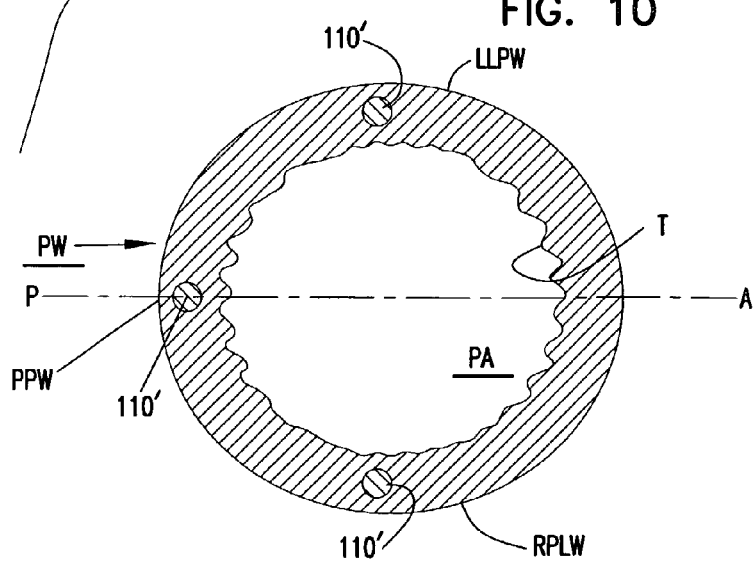
FIG. 10 is a cross-sectional view taken along section line 10—10 of FIG. 9.
Figure 11:
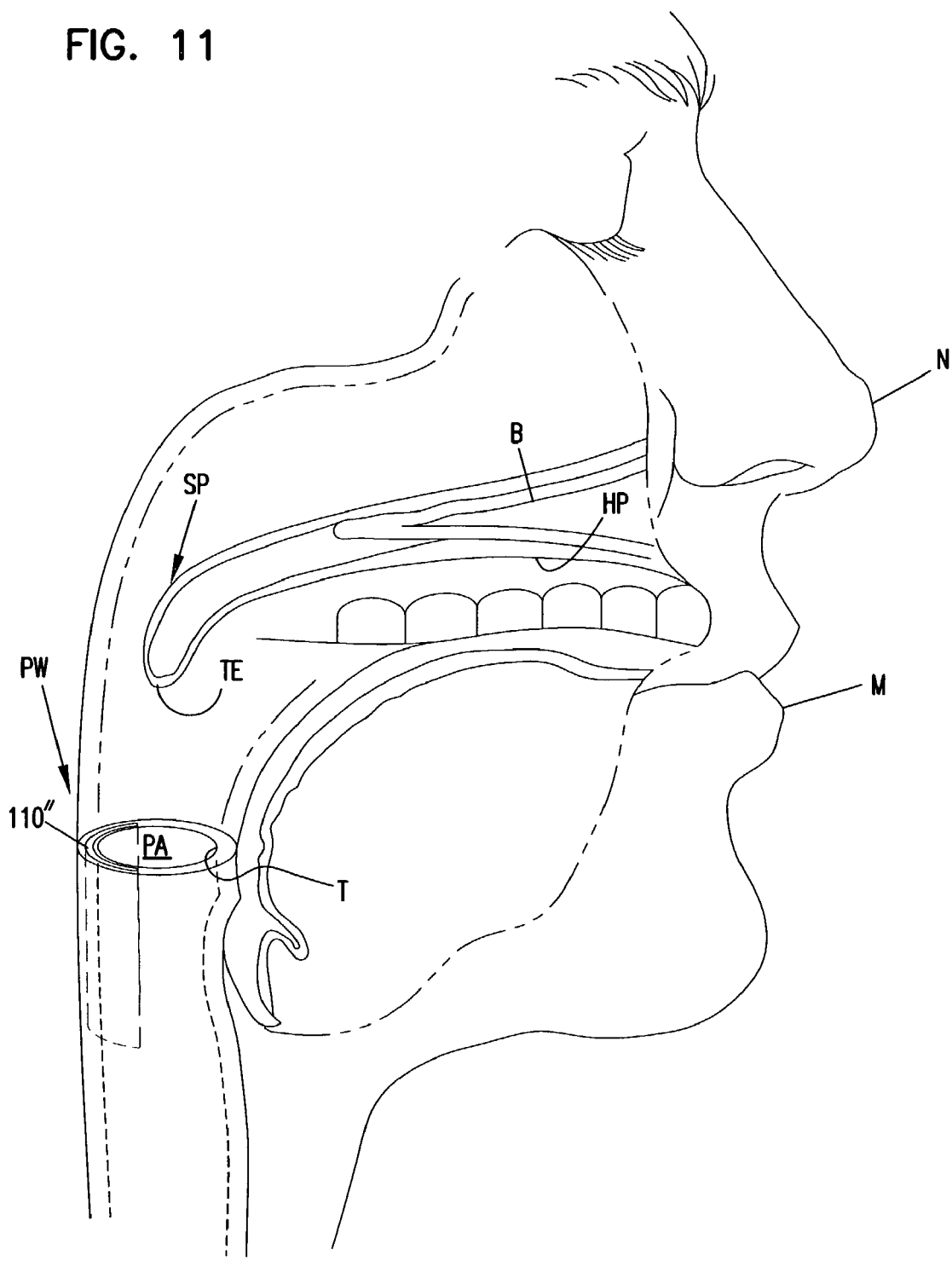
FIG. 11 is a view similar to that of FIG. 6 with a sheet placed in the pharyngeal wall.

The foregoing describes numerous embodiments of a method and apparatus to treat a pharyngeal wall. Having described the invention, alternatives and embodiments may occur to one of skill in the art. For example, while placing one or more implants 110 in the pharyngeal wall partially extending around the circumference of the pharyngeal, is a presently preferred embodiment, other alternatives exist. For example, implants 110' can be placed in pharyngeal wall parallel to the axis of the pharyngeal airway and spaced around the circumference of the pharyngeal wall as shown in FIGS. 9 and 10. Also alternatively, a sheet of polyester material 110" (or other fibrosis-inducing material) can be placed in the pharyngeal wall at least partially surrounding the axis as shown in FIG. 11. In all embodiments, any stiffness of the material and any resulting fibrosis add structural integrity to the pharyngeal wall. It is intended that such modifications and equivalents shall be included within the scope of the following claims.

What is claimed is:

1. A method for treating obstructive sleep apnea of a patient by treating a pharyngeal airway having a pharyngeal wall at least partially surrounding and defining said airway, said method comprising:

selecting an implant dimensioned so as to be implanted at a mucosal layer of said pharyngeal wall, said implant having a longitudinal dimension;

said implant having mechanical characteristics for said implant to stiffen said pharyngeal wall to resist radial collapse; and implanting said implant into said pharyngeal wall with said longitudinal dimension extending at least partially around said pharyngeal wall, transverse to a longitudinal axis of said pharyngeal airway.

2. A method according to claim 1 wherein multiple ones of said implant are implanted transverse to said longitudinal axis with said multiple ones spaced along said axis.

3. A method according to claim 2 wherein said support members are disconnected from one another.

4. A method according to claim 2 wherein said implants are implanted within a tissue layer of said pharyngeal wall.

5. A method according to claim 4 wherein said implants are imbedded within said tissue layer disconnected from a boney structure.

6. A method according to claim 1 wherein said implant is placed within a tissue layer of said pharyngeal wall.

7. A method according to claim 6 comprising:
selecting an implant having a longitudinal dimension and a narrower transverse dimension and said implant being flexible along said longitudinal dimension, said implant further dimensioned so as to not substantially increase a bulk of pharyngeal wall following implantation of said implant into said pharyngeal wall; and
implanting said implant within said pharyngeal wall with said longitudinal dimension extending in a path at least partially circumferentially surrounding said longitudinal axis of said airway.

8. A method according to claim 1 wherein said support member is elastic.

9. A method according to claim 1 wherein said support member includes a surface adapted for tissue in-growth.

10. A method according to claim 1 wherein said implant is selected for said implant, after implantation, to resist an upper airway suction closing pressure.

11. A method according to claim 10 wherein said implant is selected to resist a pressure of about 4.4 cm $H_2O$.

12. A method according to claim 1 wherein said implant is implanted at a retropalatal region of said airway.

13. A method according to claim 1 wherein said implant is implanted at a retroglossal region of said airway.

14. An apparatus for treating obstructive sleep apnea of a patient by treating a pharyngeal airway having a pharyngeal wall at least partially surrounding and defining said airway, said apparatus comprising:
an implant of bio-compatible material dimensioned so as to be embedded within said pharyngeal wall airway at a muscosal layer of said pharyngeal wall;
said implant including an array of support members;
said support members selected to stiffen said pharyngeal wall after implantation in said pharyngeal wall, to resist radial collapse of said wall.

15. An apparatus according to claim 14 wherein said implant is flexible along a longitudinal dimension.

16. An apparatus according to claim 15 wherein said implant includes a surface adapted for tissue in-growth.

17. An apparatus according to claim 16 wherein at least an outer surface of said implant is a polyester.

18. An apparatus according to claim 14 wherein said implant is elastic.

19. An apparatus according to claim 14 wherein said implant includes a radiopaque marking.

20. An apparatus according to claim 14 wherein said implant is adapted to be placed within said pharyngeal wall.

21. An apparatus according to claim 14 wherein said support members are disconnected from one another.

22. A method for treating obstructive sleep apnea of a patient by treating a pharyngeal airway having a pharyngeal wall at least partially surrounding and defining said airway, said method comprising:
selecting an implant dimensioned so as to be implanted at a mucosal layer of said pharyngeal wall, said implant having a longitudinal dimension;
said implant having mechanical characteristics for said implant to stiffen said pharyngeal wall to resist radial collapse;
selecting a site in the pharyngeal wall susceptible to collapse; and
implanting said implant into said pharyngeal wall with said longitudinal dimension extending substantially parallel to an axis of said pharyngeal airway.

23. A method according to claim 22 wherein multiple ones of said implant are implanted substantially parallel to said longitudinal axis with said multiple ones spaced along a circumference of said pharyngeal wall.

24. A method according to claim 22 wherein said implant is implanted beneath said mucosal layer.

25. A method according to claim 22 wherein said support member is elastic.

26. A method according to claim 22 wherein said support member includes a surface adapted for tissue in-growth.

27. A method according to claim 22 further comprising placing multiples of said support members spaced apart axially relative to an axis of said pharyngeal airway.

28. A method according to claim 22 wherein said support members are disconnected from one another.

29. A method for treating obstructive sleep apnea of a patient by treating a pharyngeal airway having a pharyngeal wall at least partially surrounding and defining said airway, said method comprising:
selecting an implant dimensioned so as to be implanted at a mucosal layer of said pharyngeal wall and with said implant having a surface area;
said implant having mechanical characteristics for said implant to stiffen said pharyngeal wall to resist radial collapse; and
implanting said implant into said pharyngeal wall with said surface area extending both longitudinally and transversely at least partially around an axis of said pharyngeal airway.

* * * * *